United States Patent [19]

Shinohara et al.

[11] Patent Number: 5,194,627

[45] Date of Patent: Mar. 16, 1993

[54] N-TERT-BUTYLDIALKYLSILYLMALEI-MIDE AND ITS MANUFACTURE

[75] Inventors: Toshio Shinohara, Takasaki; Motoaki Iwabuchi, Annaka, both of Japan

[73] Assignee: Shin-Etsu Chemical Co., Ltd., Tokyo, Japan

[21] Appl. No.: 882,899

[22] Filed: May 14, 1992

[30] Foreign Application Priority Data

May 14, 1991 [JP] Japan .................. 3-138477

[51] Int. Cl.$^5$ .............................................. C07F 7/10
[52] U.S. Cl. .................................................. 548/406
[58] Field of Search ........................... 548/206

[56] References Cited

U.S. PATENT DOCUMENTS

| | | | |
|---|---|---|---|
| 3,444,128 | 5/1969 | Wu ..................... | 548/406 X |
| 4,075,167 | 2/1970 | Takamizawa et al. ......... | 548/406 X |
| 4,199,511 | 4/1980 | McAfee .................. | 548/406 |
| 4,578,409 | 3/1986 | Krishnau et al. ........... | 548/406 X |
| 4,581,461 | 4/1986 | Rossi et al. ............. | 548/406 |
| 4,730,055 | 3/1988 | Rich ..................... | 548/406 |
| 4,849,490 | 7/1989 | Barthelemy .............. | 548/406 X |
| 4,923,997 | 5/1990 | Klemarczyk .............. | 548/406 X |
| 4,994,577 | 2/1991 | Hashew et al. ........... | 548/406 |
| 5,081,260 | 1/1992 | Kubota et al. ............ | 548/406 X |
| 5,084,577 | 1/1992 | Bolich ................... | 548/406 X |

FOREIGN PATENT DOCUMENTS 2142037  6/1983  United Kingdom .

OTHER PUBLICATIONS

Journal of Organic Chemistry vol. 40, No. 1, 1975, pp. 24–28; Schwartz, A. L. et al.: 'Synthesis and Properties of N-(2,3,5-Tri-o-acetyl-D-ribofuranosyl)-Maleimide'.

Chemistry Letters, No. 7, 1991, pp. 1141–1144; Matsumoto, A. et al.: 'Synthesis and Characterization of Poly(N-trialkylsilylmaleimides)s through Radical and Anionic Polymerizations'.

*Primary Examiner*—Paul F. Shaver
*Attorney, Agent, or Firm*—Oblon, Spivak, McClelland, Maier & Neustadt

[57] ABSTRACT

An N-tert-butyldialkylsilylmaleimide represented by the following general formula:

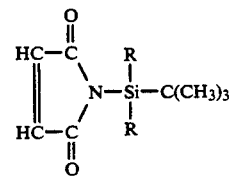

wherein R's represent $C_1$ to $C_5$ alkyl groups which may be the same or different and a method of producing the compound. Said N-tert-butyldialkylsilylmaleimide is useful as a silylating agent, which does not produce hydrogen chloride or the like as a by-product and therefore does not require to use a neutralizing agent additionally. Further this compound is useful as a compound which provides a maleimido group.

7 Claims, 1 Drawing Sheet

N-TERT-BUTYLDIALKYLSILYLMALEIMIDE AND ITS MANUFACTURE

BACKGROUND OF THE INVENTION

1. Field of the Invention

The present invention relates to an N-tert-butyldialkylsilylmaleimide which is a new organosilicon compound.

2. Description of the Prior Art

As an organosilicon compound having a maleimide skeleton, N-trimethylsilylmaleimide having the following chemical formula (1) is known [J. Org. Chem., 40, 25 (1975)]:

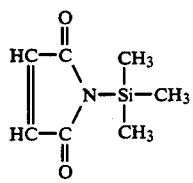
(1)

Since this N-trimethylsilylmaleimide reacts with an organic compound having active hydrogen, it is useful as a silylating agent. Further, as an organosilicon compound having a group represented by the following chemical formula (2):

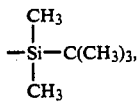
(2)

tert-butyldimethylsilyl chloride having the following chemical formula (3):

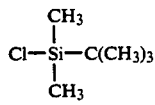
(3)

is known. This tert-butyldimethylsilyl chloride is useful as a silylating agent.

However, since the trimethylsilyl group possessed by the N-trimethylsilylmaleimide of the chemical formula (1) is low in bulkiness of the organic group in comparison with the tert-butyldimethylsilyl group which is attracting attention recently, it has a defect that the protective effect of the silylated site against other reagents is low.

Further, in the silylating reaction wherein the above compound having the chemical formula (3) is used, since hydrogen chloride is formed as a by-product, a neutralizing agent must be used additionally.

SUMMARY OF THE INVENTION

Therefore, an object of the present invention is to provide a new organosilicon compound useful as a silylating agent and free from the above defects.

That is, the present invention provides an N-tert-butyldialkylsilylmaleimide represented by the following general formula (I):

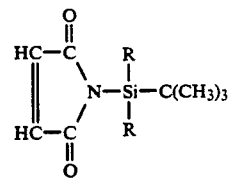
(I)

wherein R's, which may be the same or different, each represent an alkyl group having 1 to 5 carbon atoms.

The N-tert-butyldialkylsilylmaleimide is useful as a silylating agent, which does not produce hydrogen chloride or the like as a by-product and therefore does not require to use a neutralizing additionally. This compound is also useful as a compound which provides a maleimido group.

BRIEF DESCRIPTION OF DRAWINGS

In the attached drawing.

Figure 1:
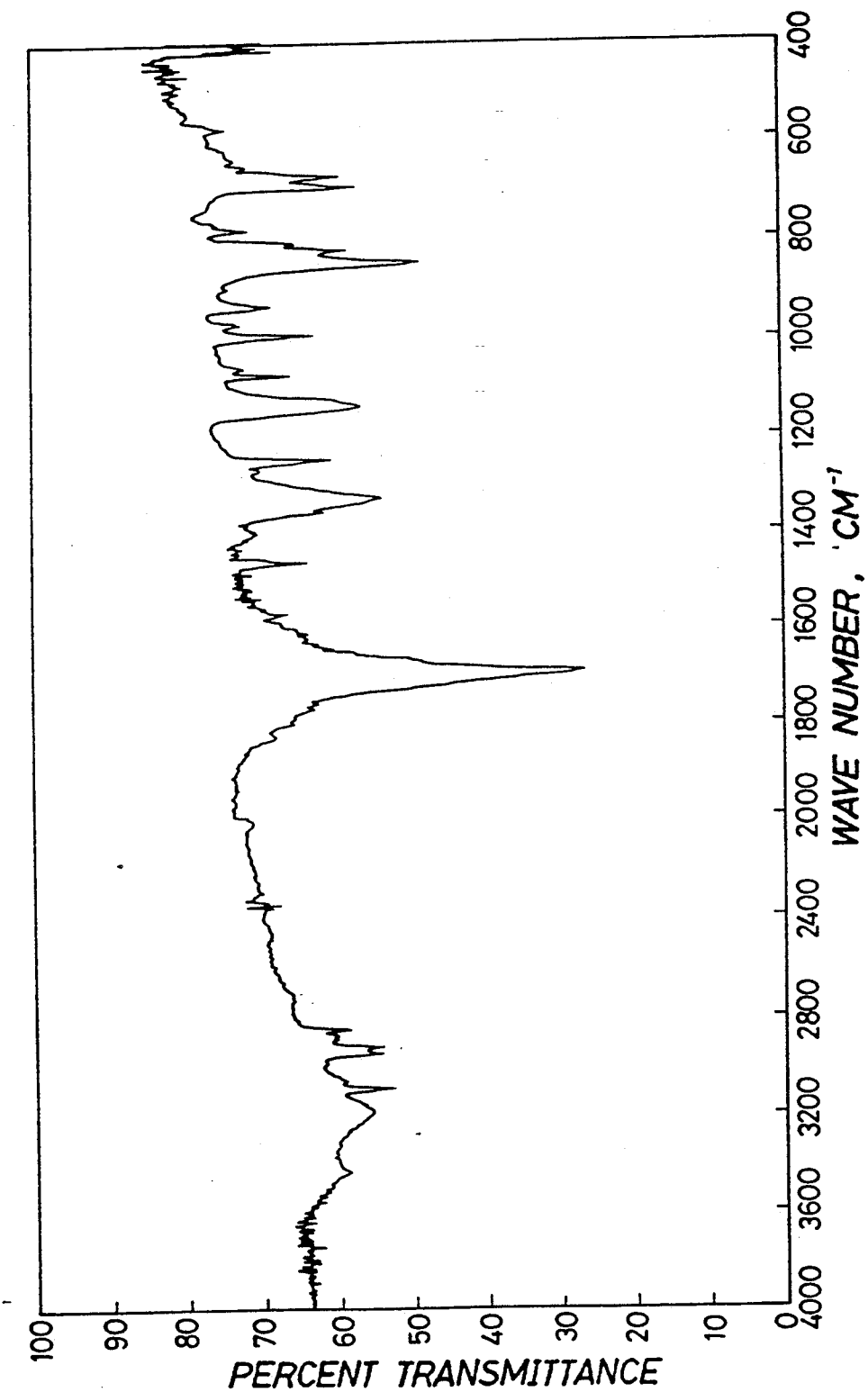
FIG. 1 is the infrared absorption spectrum of the present compound obtained in Example 1.

DETAILED DESCRIPTION OF PREFERRED EMBODIMENT N-tert-butylDIalkylsilylmaleimides The N-tert-butyldialkylsilylmaleimide according to the present invention has, in the compound, two lower-alkyl groups represented by R in said general formula (I).

The two lower alkyl groups R may be the same or different and the alkyl group R has 1 to 5 carbon atoms, typically 1 to 3 carbon atoms. Specifically, the alkyl group R represents, for example, a methyl group, an ethyl group, a propyl group, or an isopropyl group, typically a methyl group. If said compound is used as a silylating agent, most preferably R is a methyl group.

The N-tert-butyldialkylsilylmaleimide containing the groups mentioned above include, for example, compounds represented by the following chemical formulas:

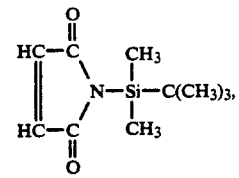

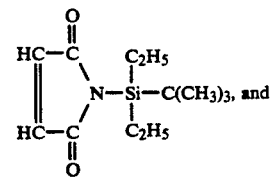

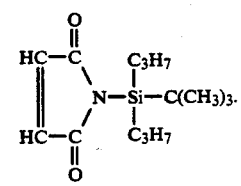

Process of the Preparation

The present N-tert-butyldialkylsilylmaleimide can be produced, for example, by a process comprising the steps of:

(a) reacting an alkali metal hydride and maleimide in an organic solvent to form an alkali metal maleimide and (b) reacting said alkali metal maleimide and a tert-butyldialkylsilyl halide represented by the formula (II):

wherein R has the same meaning as defined above and X represents a halogen atom, in an organic solvent.

Step (a)

In the step (a), an alkali metal hydride and maleimide are reacted. The alkali metal contained in the alkali metal hydride includes, for example, lithium, sodium, and potassium, with sodium being preferred.

To react the alkali metal hydride and maleimide, generally the alkali metal hydride is used in an amount about 1 to 2 times the equivalent amount to maleimide. At that time, it is recommended that an alkali metal hydride and maleimide are dissolved in organic solvents respectively. The concentration of the alkali metal hydride solution may be in the range of 0.01 to 50 wt. %, preferably 10 to 20 wt. %. As the organic solvent used for preparing the alkali metal hydride solution, a hydrocarbon solvent and an ether solvent are preferable. As the hydrocarbon solvent, a saturated hydrocarbon having 5 to 10 carbon atoms is preferable. For example, a linear hydrocarbon such as pentane, hexane, heptane, octane, nonane, and decane can be mentioned with preference given particularly to pentane. On the other hand, the ether solvent includes, for example, diethyl ether, dibutyl ether, and tetrahydrofuran, with preference given particularly to tetrahydrofuran. Prior to dissolving the alkali metal hydride in an organic solvent, it is recommended that the alkali metal hydride is washed with the same organic solvent.

The maleimide solution desirably contains 0.01 to 10M, preferably 1 to 5M, of maleimide. The organic solvent to be used is preferably the ether solvents mentioned above.

The reaction of the alkali metal hydride and maleimide may be carried out, for example, by adding a maleimide solution dropwise to an alkali metal hydride solution. In this case, the temperature of the reaction solution is preferably −50° C. to +20° C. The time required for the addition is preferably 0.1 to 5 hours.

Step (b)

In the step (b), the alkali metal maleimide obtained in the step (a) and a tert-butyldialkylsilyl halide are reacted to form an N-tert-butyldialkylsilylmaleimide. The tert-butyldialkylsilyl halide used herein includes, for example, the chloride, bromide, and iodide, with the chloride being generally preferable. Similarly to the reaction in the step (a), in this reaction it is recommended that after the tert-butyldialkylsilyl halide is dissolved in an organic solvent, it is reacted. In this case, the concentration of the tert-butyldialkylsilyl halide in the solvent is preferably 0.01 to 10M, more preferably 1 to 5M. The solvent to be used is preferably the hydrocarbon solvents and ether solvents mentioned above.

The reaction between an alkali metal maleimide and a tert-butyldialkylsilyl halide may be carried out by adding the tert-butyldialkylsilyl halide solution dropwise to the solution obtained in the step (a). The tert-butyldialkylsilyl halide is used desirably in an amount generally 1 to 2 times the equivalent amount to the alkali metal maleimide. The temperature of the reaction solution is preferably −50° C. to +20° C. The time required for the addition is preferably 0.1 to 5 hours.

The solution obtained after the completion of the step (b) contains, in addition to the intended N-tert-butyldialkylsilylmaleimide, generally various by-products. Therefore, the N-tertbutyldialkylsilylmaleimide in the solution is required to be purified. The purification can be carried out, for example, as follows.

After the solution obtained in the step (b) is matured at about 20° C. for 1 to 3 hours, the solution is filtered under pressure to eliminate sodium chloride which is a by-product. Then the resulting solution is subjected to distillation under reduced pressure to remove the solvents. To the residue, a hydrocarbon solvent such as pentane in an amount of 100 to 1,000 wt. % of the amount of the raw material maleimide used is added, and the obtained solution is filtered to eliminate unreacted maleimide. The resulting filtrate is condensed and is distilled under reduced pressure to obtain a fraction. The fraction consists of the N tert-butyldialkylsilylmaleimide isolated.

Uses

Since the present N-tert-butyldialkylsilylmaleimide has an Si-N bond therein that can be readily hydrolized, the compound can be used as a silylating agent for a silylation reaction. In that case, unlike the silylation reaction where the above tert-butyldimethylsilyl chloride is used, the reaction is advantageous in that a neutralizing agent is not required additionally.

Since the tert-butyldialkylsilyl group possessed by the present N-tert-butyldialkylsilylmaleimide is bulky in its steric structure, the compound can be used as a maleimide group donative compound.

EXAMPLES Example 1

After 18.6 g of oily sodium hydride which contained 60 wt. % of sodium hydride [11.2 g (0.467 mol) in terms of sodium hydride] was washed with 50 ml of dry pentane three times, the oily sodium hydride was dissolved in 118 ml of dry tetrahydrofuran to form a suspension. On the other hand, 37.7 g (0.388 mol) of maleimide was dissolved in 117 ml of tetrahydrofuran to obtain a solution of the maleimide in the tetrahydrofuran.

While the temperature of the sodium hydride suspension was kept at 20° C., the solution of the maleimide in tetrahydrofuran was added dropwise thereto over 1 hour.

While the temperature of the obtained solution was kept at 20° C., a solution of 58.4 g (0.388 mol) of tert-butyldimethylsilyl in 77 ml of dry tetrahydrofuran was added dropwise thereto over 20 min.

After the thus obtained solution was matured for 2 hours with the temperature kept at 20° C., the solution was filtered under pressure in a nitrogen atmosphere to eliminate sodium chloride which was a by-product. The filtrate was distilled under reduced pressure to eliminate the tetrahydrofuran. 250 g of heptane was added to the obtained residue followed by filtration under reduced pressure, and the filtrate was condensed and then was distilled under a reduced pressure of 80 mm Hg at a temperature of 153° C. to obtain 20 g of a fraction.

Identification

To identify the fraction, analysis by gas chromatography and measurement of the $^1$H-NMR, infrared spectrum, and melting point were carried out. The results are shown below.

Analysis by gas chromatography

It was confirmed that the obtained fraction is a single component product.

$^1$H-NMR
In CDCl$_3$, the internal standard: Si(CH$_3$)$_4$
δ (ppm)
6.50 (s, —CH=CH—, 2H)
0.76 (s, —C(CH$_3$)$_3$, 9H)
0.27 (s, —CH$_3$, 6H)
Infrared spectrum
The infrared spectrum is shown in FIG. 1.
Characteristic absorptions:
=C—H 3,100 cm$^{-1}$
—C—H 2,900 cm$^{-1}$
C=O 1,700 cm$^{-1}$
Melting point
67° to 68° C.

From the above results, it was identified that the fraction is N-tert-butyldimethylsilylmaleimide having the following chemical formula:

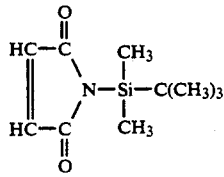

(yield: 24 %).

Reference Example

To 25 g (0.258 mol) of maleimide were added 38.8 g (0.258 mol) of tert-butyldimethylsilyl chloride, 26.2 g (0.259 mol) of triethylamine, and 773 ml of dry benzene followed by refluxing for 48 hours. The resulting solution was analyzed by gas chromatography, which showed that no N-tert-butyldimethylsilylmaleimide was formed in the solution.

Application Example 1

To 0.52 g (0.166 mol) of methanol were added 3.5 g (0.166 mol) of N-tert-butyldimethylsilylmaleimide and 0.0002 g (0.004 mmol) of ammonium chloride and the resulting solution was stirred for 12 hours with the temperature kept at 40° C. Thereafter, the solution was analyzed by gas chromatography, which showed that 42 % of the methanol was tert-butyldimethylsilylated and an organosilicon compound represented by the following chemical formula:

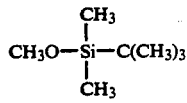

was formed. The chemical structure was confirmed by analysis by gas chromatography and measurement of the $^1$H-NMR and infrared spectrum.

We claim:
1. An N-tert-butyldialkylsilylmaleimide represented by the following general formula:

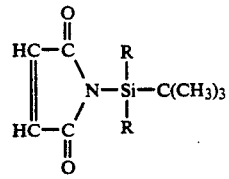

wherein R's, which may be the same or different, each represent an alkyl group having 1 to 5 carbon atoms.

2. An N-tert-butyldialkylsilylmaleimide as claimed in claim 1, wherein, in the general formula (I), R is selected from the group consisting of a methyl group, an ethyl group, a propyl group, and an isopropyl group.

3. An N-tert-butyldialkylsilylmaleimide as claimed in claim 2, wherein, in the general formula (I), R is a methyl group.

4. An N-tert-butyldialkylsilylmaleimide as claimed in claim 1, represented by the following formula:

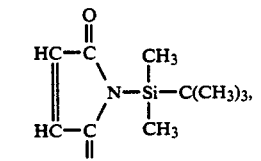

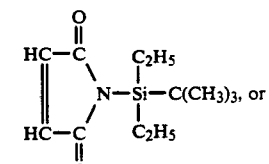

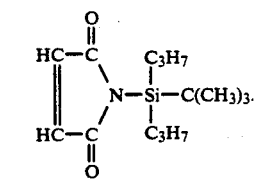

5. A method of producing an N-tert-butyldialkylsilylmaleimide as claimed in claim 1, comprising the steps of:
(a) reacting an alkali metal hydride and maleimide in an organic solvent to form an alkali metal maleimide and
(b) reacting said alkali metal maleimide and a tert-butyldialkylsilyl halide represented by the formula (II):

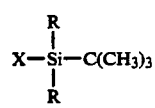

wherein R has the same meaning as defined above and X represents a halogen atom, in an organic solvent.

6. A method as claimed in claim 5, wherein said alkali metal hydride is sodium hydride.

7. A method as claimed in claim 5, wherein said compound represented by the formula (II) is a tert-butyldialkylsilyl chloride.